US008691183B2

(12) United States Patent
Heckl

(10) Patent No.: US 8,691,183 B2
(45) Date of Patent: Apr. 8, 2014

(54) MEANS FOR THE DETECTION AND TREATMENT OF PROSTATE CELLS

(75) Inventor: Stefan Heckl, Tuebingen (DE)

(73) Assignee: Eberhard-Karls-Universitaet Tuebingen Universitaetsklinikum, Tuebingen (DE)

( * ) Notice: Subject to any disclaimer, the term of this patent is extended or adjusted under 35 U.S.C. 154(b) by 0 days.

(21) Appl. No.: 13/023,136

(22) Filed: Feb. 8, 2011

(65) Prior Publication Data

US 2011/0165065 A1     Jul. 7, 2011

Related U.S. Application Data

(63) Continuation of application No. PCT/EP2009/005882, filed on Aug. 13, 2009.

(30) Foreign Application Priority Data

Aug. 13, 2008   (DE) .......................... 10 2008 039 417

(51) Int. Cl.
*A61K 51/00* (2006.01)
*A61M 36/14* (2006.01)

(52) U.S. Cl.
USPC ........................................................ 424/1.11

(58) Field of Classification Search
USPC .................................. 424/400, 1.11
See application file for complete search history.

(56) References Cited

FOREIGN PATENT DOCUMENTS

| DE | 10 2006 008074 | 8/2007 |
| WO | 2004/033496 | 4/2004 |
| WO | 2007/030571 | 3/2007 |

OTHER PUBLICATIONS

Du (Biochemistry 1994, 33, 4812-4819).*
Ashida, Shingo, et al., "Molecular Features of the Transition from Prostatic Intraepithelial Neoplasia (PIN) to Prostate Cancer: Genome-wide Gene-expression Profiles of Prostate Cancers and PINs", Cancer Research, vol. 64, pp. 5963-5972 (2004).
Ben-Arie, Nissim, et al., "Olfactory receptor gene cluster on human chromosome 17: possible duplication of an ancestral receptor repertoire," Hum. Mol. Genet. vol. 3, pp. 229-235 (1994).
Harisinghani, M.G., et al., "Ferumoxtran-10-Enhanced MR Lymphangiography: Does Contrast-Enhanced Imaging Alone Suffice for Accurate Lymph Node Characterization?" Am. J. Roentgenol; 186(1): 144-8 (2006).
Jacquier, Valerie, et al., "Characterization of an extended receptive ligand repertoire of the human olfactory receptor OR17-40 comprising structurally related compounds," Journal of Neurochemistry, 2006, 97, pp. 537-544.
Lee, Dennis K., et al., "Discovery and mapping of ten novel G protein-coupled recptor genes," Gene, vol. 275, pp. 83-91 (2001).
Messing, Edward M., M.D., et al., "Immediate Hormonal Therapy Compared with Observation After Radical Prostatectomy and Pelvic Lymphadenectomy in Men with Node-Positive Prostate Cancer," The New England Journal of Medicine, 341 (24): 1781-1788 (1999).
Spehr, et al. (2004), "Dual Capacity of a Human Olfactory Receptor," Curr. Biol. vol. 14, No. 19, R832-3.
Spehr, Marc, et al., "Identification of a Testicular Odorant Receptor Mediating Human Sperm Chemotaxis," Science, vol. 299, Mar. 28, 2003.
Walsh, P.C. (2002), "Surgery and the Reduction of Mortality From Prostate Cancer," N. Engl. J. Med.; 347 (11): 839-840.
Weigle, Bernd, et al., "D-GPCR: a novel putative G protein-coupled recptor overexpressed in prostate cancer and prostate," Biochemical and Biophysical Research Communications, vol. 322, pp. 239-249 (2004).
Xu, Li, et al., "Quantitative Expression Profile of PSGR in Prostate Cancer," Prostate Cancer and Prostatic Diseases, vol. 9, 2006, pp. 56-61.

* cited by examiner

*Primary Examiner* — David J Blanchard
*Assistant Examiner* — Devang Thakor
(74) *Attorney, Agent, or Firm* — Casimir Jones SC

(57) ABSTRACT

The present invention relates to a composition for the detection and the treatment of prostate cells and to methods for the diagnostic and therapeutic treatment of a human being using the composition according to the invention.

14 Claims, 6 Drawing Sheets

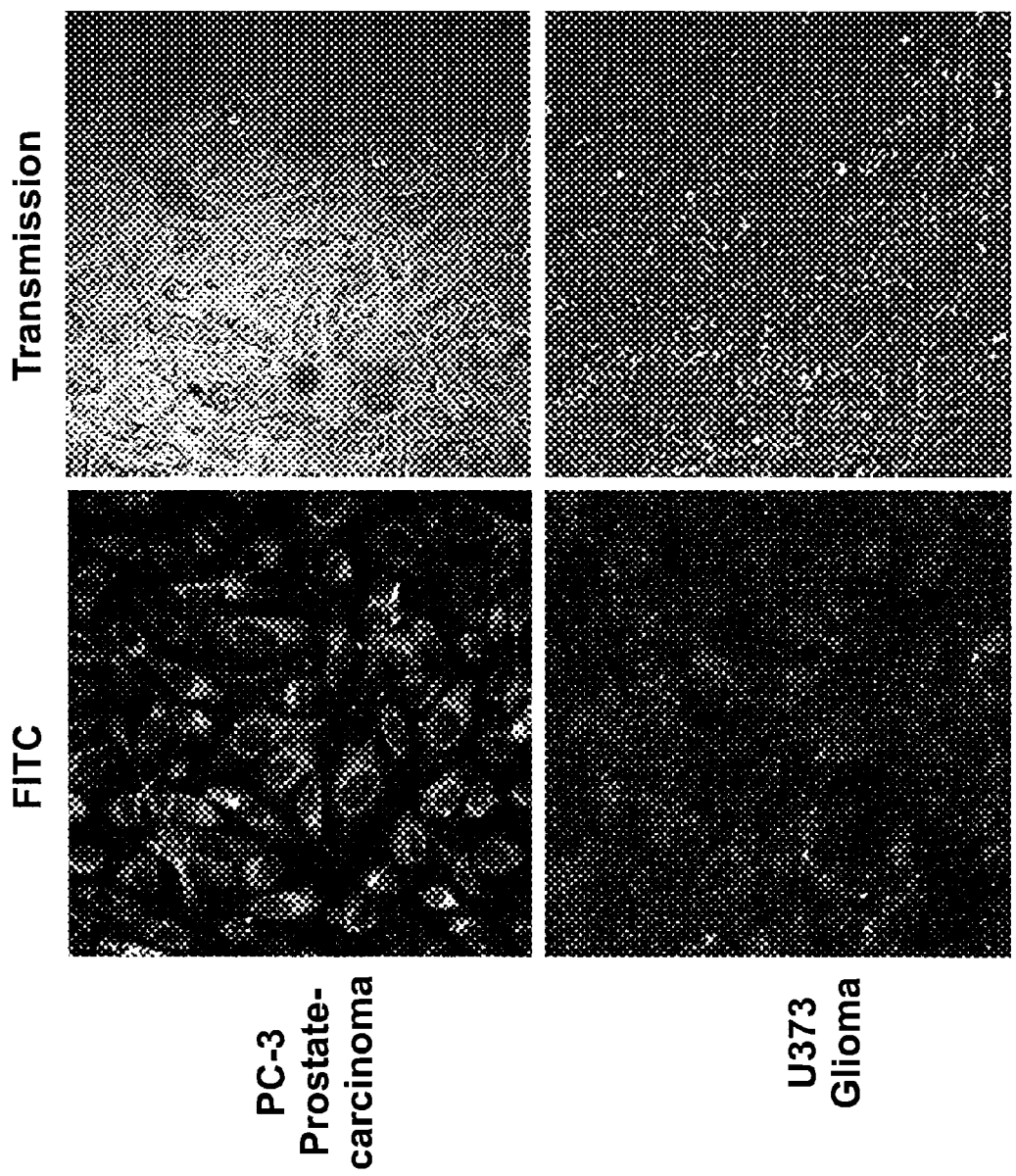

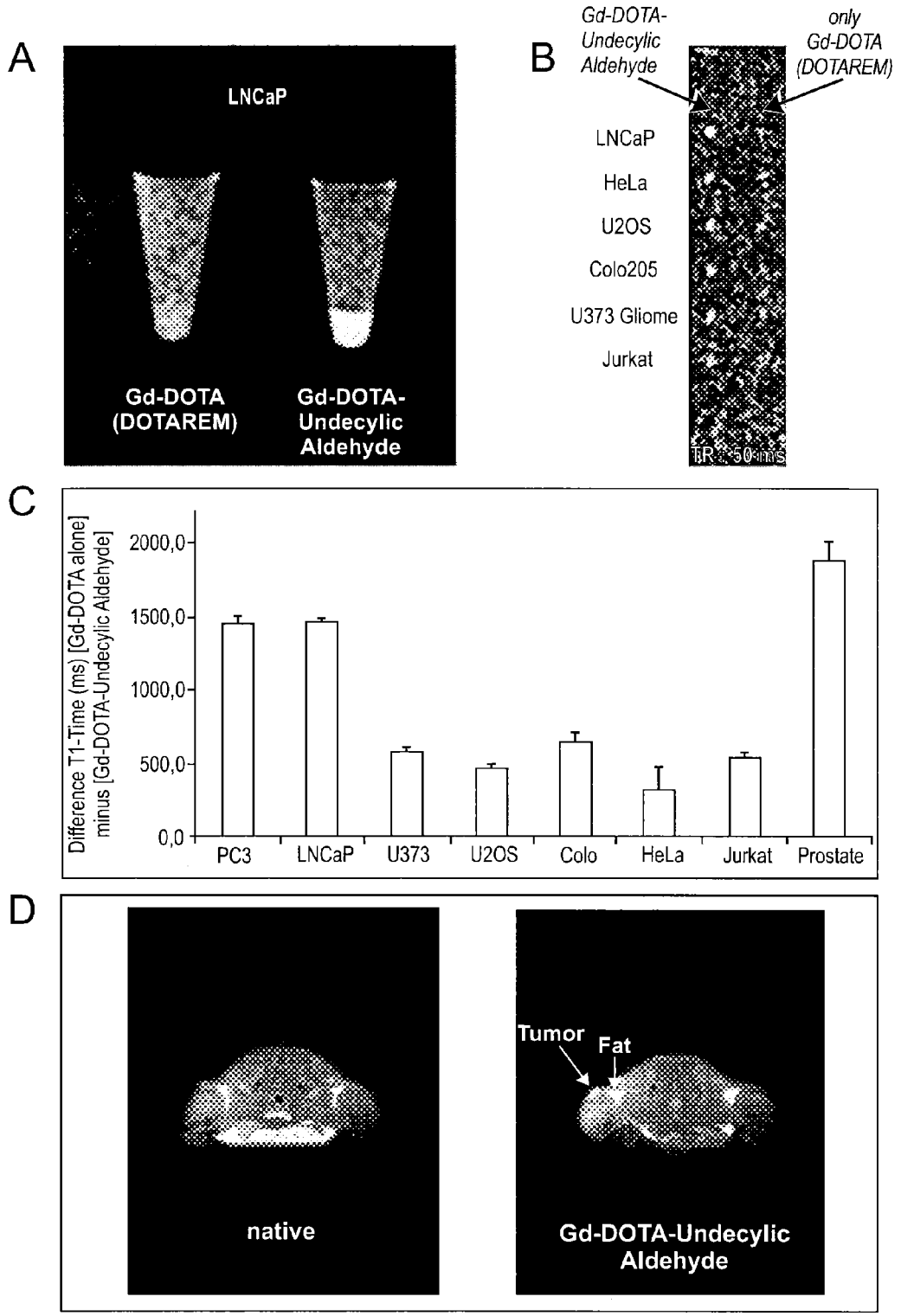

Fig. 5A Frozen Section (Prostate Carcinoma PC 3)
Fusion    Rhodamine
20 Min.
180 Min.
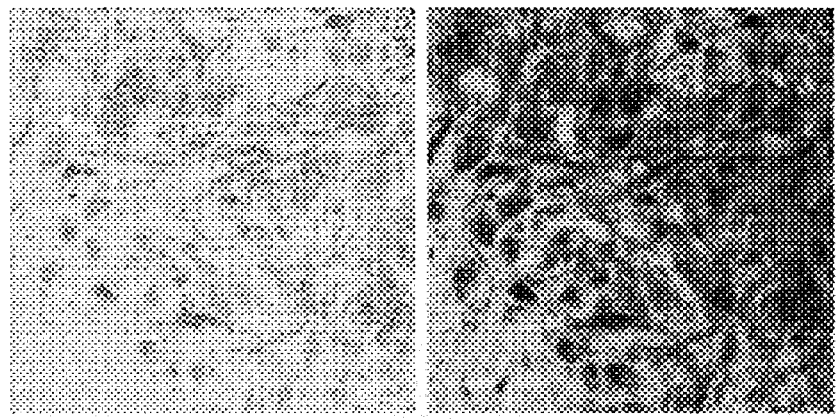
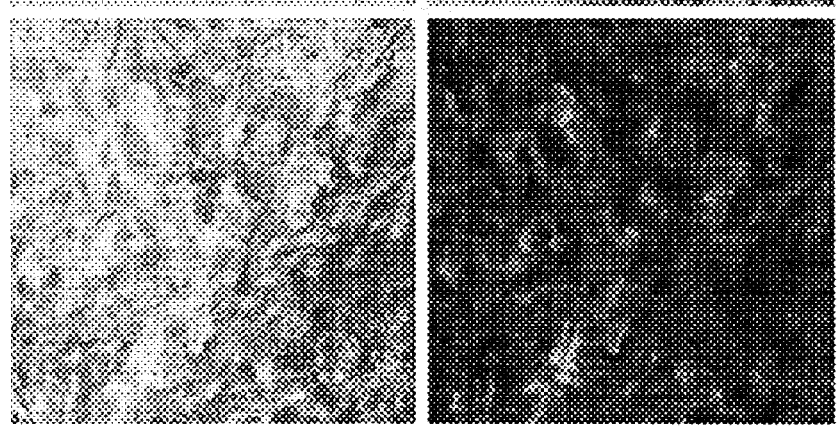
Fig. 5B Touch Print (Prostate Carcinoma PC 3)
Fusion    Rhodamine
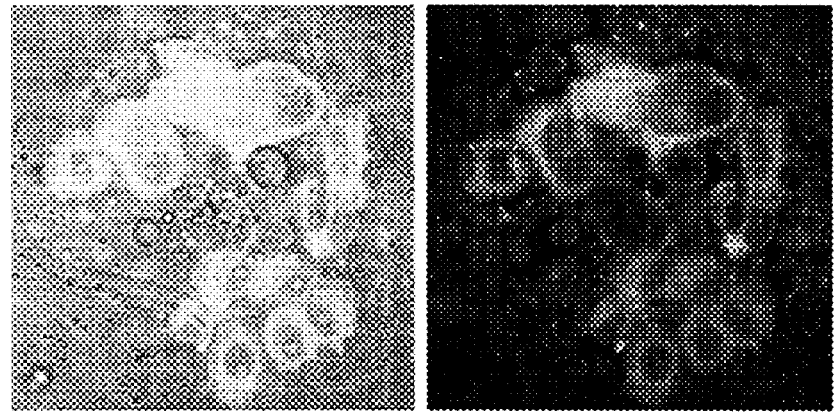

MEANS FOR THE DETECTION AND TREATMENT OF PROSTATE CELLS

CROSS-REFERENCE TO RELATED APPLICATIONS

This application is a continuation of copending International Patent Application PCT/EP2009/005882 filed on Aug. 13, 2009 and designating the United States, which was not published under PCT Article 21(2) in English, and claims priority of German Patent Application DE 10 2008 039 417.3 filed on Aug. 13, 2008, which is incorporated herein by reference.

BACKGROUND OF THE INVENTION

1. Field of the Invention

The present invention relates to a composition for the identification and the treatment of prostate cells as well as to methods for the diagnostic and therapeutic treatment of a living being using the composition according to the invention.

2. Related Prior Art

Compositions for the identification and the treatment of prostate cells are generally known in the art.

The prostate carcinoma is a malignant tumor disease which originates from the gland tissue of the prostate. In Germany almost three out of one hundred men die from prostate carcinoma. The prostate carcinoma, therefore, belongs to the most frequent cancer diseases of men. Within the group of men died from cancer it is responsible for about 10% of the deaths and, therefore, is the third-most deadly cancer disease after lung and colon cancer.

The precondition for a therapeutic treatment of the prostate carcinoma is a reliable diagnosis. It is in particular decisive whether an affected patient has already a lymph node metastasis; Messing E. M. et al. (1999), Immediate hormonal therapy compared with observation after radical prostatectomy and pelvic lymphadenectomy in men with node-positive prostate cancer. N. Engl. J. Med.; 341 (24): 1781-1788; Walsh P. C. (2002), Surgery and the reduction of mortality from prostate cancer. N. Engl. J. Med.; 347 (11): 839-840.

The identification or demarcation of prostate carcinoma metastases in lymph nodes occurs as a "negative image" by means of the magnetic resonance tomography (MRT). For doing so iron particles are intravenously injected; cf. Harisinghani M. G. et al. (2006), Ferumoxtran-10-enhanced MR lymphangiography: does contrast-enhanced imaging alone suffice for accurate lymph node characterization? Am. J. Roentgenol.; 186 (1): 144-8. The iron particles are taken up by the reticuloendothelial system (RES) of the lymph node, however not by the prostate carcinoma metastasis itself since in this position the RES is displaced. In the T2-weighted MRT images the RES can be seen in dark because of the uptaken iron particles, however the prostate carcinoma metastasis remains in light.

However, also in areas of inflammation processes, fat deposits and fibroses a displacement of the RES can be found also resulting in light areas in the magnetic resonance tomography and thus appear as metastases like structures. Further, with this method it cannot be distinguished between metastases of different origins, i.e. prostate, colon, bladder etc., since with this method only the RES however not the cancer cells itself can be visualized.

SUMMARY OF THE INVENTION

Against this background the object underlying the invention is to provide a new composition by means of which prostate cells, in particular the prostate carcinoma cells and such cells which are present in the lymph nodes, can be identified in a reliable and "positive" manner This problem is solved by the provision of such a composition which comprises a ligand of the lilly-of-the-valley odorant receptor (OR17-4), preferably of the human variant (hOR17-4) thereof.

This finding was surprising. So far it was assumed that odorant receptors are predominantly found in the nose. The existence of odorant receptors also in other tissues has only occasionally been described.

For example Spehr et al. (2003), Identification of a testicular odorant receptor mediating human sperm chemotaxis, Science Vol. 299, pages 2054-2058, and Spehr et al. (2004), Dual capacity of a human olfactory receptor, Curr. Biol. Vol. 14, No. 19, R832-3, describe the expression of the lilly-of-the-valley odorant receptor hOR17-4 on sperms.

In the WO 2004/033496 it is therefore suggested to use a ligand for the human lilly-of-the-valley odorant receptor hOR17-4 as a contraception or a conception promoting medicament.

Only few odorant receptors have so far been found in the prostate, as e.g. the OR 51 E2 [Ashida et al. (2004), Molecular features of the transition from prostatic intraepithelial neoplasia (PIN) to prostate cancer: genome-wider gene-expression profiles of prostate cancers and PINs. Cancer Res. Vol. 64, pages 5963-5972], the Dresden G protein-coupled receptor (D-GPCR) [Weigle et al. (2004), D-GPCR: a novel putative G protein-coupled receptor overexpressed in prostate cancer and prostate. Biochemical and Biophysical Research Communications, Vol. 322, pages, 239-249] or the G protein-coupled receptor 92 (GPR95) [Lee et al. (2001), Discovery and mapping of ten novel G protein-coupled receptor genes. Gene, Vol. 275, pages 83-91].

Against this background the finding of the inventor that the lilly-of-the-valley odorant receptor OR17-4 or hOR17-4, respectively, is expressed in the prostate, was very surprising.

It was also surprising that prostate carcinoma cells very strongly express the lilly-of-the-valley odorant receptor OR17-4 or hOR17-4, respectively. Therefore, by means of the composition according to the invention not only prostate cells can be identified, furthermore it is possible to distinguish between healthy and degenerated prostate cells. A degenerated prostate cell binds essentially more of the composition according to the invention than a healthy prostate cell.

As the inventor was able to realize the composition according to the invention binds to the cell surface of prostate cells and is then absorbed into the cytoplasm.

As the inventor was further able to realize the composition according to the invention is only absorbed into the prostate cells but, except into the olfactory organs, not into the tissues of the muscles, testicles, heart, colon, lymph nodes, seminal vesicles, spleen, skin, brain, and lung. Remarkably, the composition according to the invention is also not absorbed into other malignant cells, for example of a colon carcinoma, glioma, osteosarcoma, cervix carcinoma, and lymphoma.

Hence, the inventor provides a composition for the first time, by means of which prostate cells, including prostate carcinoma cells can be highly selectively and "positively" identified.

The lilly-of-the-valley odorant receptor is officially referred to as OR17-4, the human variant is referred to as hOR17-4. In matters of nomenclature it is referred to the publication of Ben-Arie et al. (1994), Olfactory receptor gene cluster on human chromosome 17: possible duplication of an ancestral receptor repertoire, Hum. Mol. Genet. Vol. 3, pages 229-235. A synonymous designation for hOR17-4 is OR1D2.

With this designation the gene sequence is published in the GenBank data base under the GenBank accession No. NM_002548 or the EMBL accession No. AF087917; the entire gene sequence is incorporated into the present application by reference. The lilly-of-the-valley odorant receptor belongs to the group of G protein-coupled receptors.

A "ligand" refers to such a compound which can bind under stringent conditions selectively and specifically to the lilly-of-the-valley odorant receptor OR17-4 or hOR17-4, respectively.

According to the invention a "composition" refers to any composition which at least comprises the ligand of the human lilly-of-the-valley odorant receptor, however, if applicable, can contain further compounds such as a detectable marker or a diagnostically or pharmaceutically acceptable carrier. Such carriers are comprehensibly disclosed in the prior art, e.g. in Kibbe et al. (2000), Handbook of Pharmaceutical Excipients, 3rd Edition, American Pharmaceutical Association and Pharmaceutical Press. The content of this publication is incorporated into the present application by reference. Preferred compositions are detection compositions, medicaments, diagnostic and therapeutic compositions.

According to the invention, "identification" refers to any measure that serves to the detection of prostate cells or prostate carcinoma cells.

According to the invention, "treatment" refers to any measure by means of which it is acted on the prostate cells, in particular the prostate carcinoma cells. In particular, the treatment encompasses the therapeutic action on prostate carcinoma cells.

The object underlying the invention is herewith completely achieved.

According to the invention it is preferred if the ligand is selected from the group consisting of: undecylic aldehyde, 3-phenyl-2-propenal(cinnamaldehyde), octanal, bourgeonal, benzaldehyde, phenylacetaldehyde, 3-phenylpropanal, 3-phenylbutyl aldehyde, 4-phenylbutyraldehyde, canthoxal, cyclamal, floralazone, lilial, (4-ter-butylphenoxy)acetaldehyde, p-anisyl-formate, piperonylacetate, cinnamyl alcohol, hydrocinnamaldehyde, methylcinnamaldehyde, methyl-hydro-cinnamaldehyde, methylnonylaldehyde, phenetyl alcohol, phenylpropanol, methylcinnamaldehyde, isobutyraldehyde, helional, lyral, methyl-phenyl-pentanal, cyclosal, foliaver, trimethylmethane, trifernal, piperonal, isovaleraldehyde, (4-hydroxyphenyl)-butan-2-on (raspberry ketone), vanillin, safrole, heptanal, anethole, 5-phenylvalderaldehyde, isopropylbenzene, 3-phenylbutyl alcohol and 3-phenylpropionic acid.

The before-mentioned compounds are examples of ligands of the lilly-of-the-valley odorant receptor OR17-4 or the human variant hOR17-4, respectively, which are especially suited for the production of the composition according to the invention. It is understood that the ligands can be modified to e.g. couple a further compound to the ligand, such as a marker. A suitable modification can for example consist of the attachment of an amino group, e.g. to form aminoundecylic aldehyde, aminobourgeonal, aminocinnamaldehyde, or aminobenzaldehyde. Furthermore, several amino acids can be provided. Correspondingly modified ligands are also encompassed by the invention; cf. also V. Jacquier et al. (2006), Journal of Neuroscience, Volume 97, pages 537-544 and WO 2004/033496.

According to the invention it is preferred if the composition further comprises a marker detectable by means of an imaging method.

According to the invention imaging methods comprise all apparatus-supported methods by means of which physiological or medical findings or physical or chemical phenomena can be visualised. To such methods belong the fluorescence microscopy, magnetic resonance tomography (MRT), radiography, computer tomography, positron emission tomography (PET), scintigraphy, single photon emission computed tomography (SPECT), sonography, mass spectrometry etc. According to the invention, any marker is encompassed which is detectable in at least one of the before-mentioned methods.

This method has the advantage that the composition according to the invention is provided as a diagnostic composition. Due to the high selectivity of the composition according to the invention by this further development for the first time prostate cells or prostate carcinoma cells, respectively, can be positively imaged even in lymph nodes. So far this can only be realized in a very unspecific manner by means of a negative image by the administration of iron particles where also areas are stained which do not contain prostate cells.

It is further preferred if such a marker is used which is detectable by means of the fluorescence microscopy and preferably selected from: fluorescein isothiocyanate (FITC), rhodamine, rhodamine isothiocyanate (RITC), sulforhodamine, dansyl chloride, fluorescamine, green fluorescent protein (GFP), ethidium bromide, 4',6-diamidino-2-phenylindole (DAPI), coumarin, luciferase, phycoerythrin (PE), Cy2, Cy3.5, Cy5, Cy7, texas red, alexa fluor, fluor X, red 613, BODIPY-FL, TRITC, DS red, GFP, DS red.

The before identified markers have been proven of value in the molecular diagnostics and which can be bound to the ligand by standard methods. For doing so, it might be necessary to modify the detectable marker, e.g. by providing sulphur and/or amino groups, e.g. to obtain a sulforhodamine-sulfonamido compound or FITC-βAla-compounds. Such modified markers are encompassed by the invention.

The marker can further be a marker detectable by means of magnetic resonance tomography (MRT), preferably a complexing agent for metals and a complexed metal, including gadolinium (Gd), europium (Eu), gallium (Ga), manganese (Mn), iron (Fe), Yttrium (Y) and its isotopes. In this context it is further preferred if the complexing agent for metals is selected from the group consisting of: tetraazacyclododecane tetraacetic acid (DOTA), diethylenetriaminepentaacetic acid (DTPA), BOPTA, EOB-DTPA, DTPA-DMA, HP-DOBA, DTPA-BMEA, HIDA, DTDP, porphyrine, texaphyrine, TEKES, fullerene, crown ether.

This method has the advantage that a contrast medium for the magnetic resonance tomography (MRT) is provided by means of which prostate cells and prostate carcinoma cells, including such being in the lymph nodes, can be imaged in a reliable manner. As a result, a long lasting need is fulfilled since, so far, such contrast media suitable for the imaging of prostate carcinoma metastases do not exist. These contrast media allow a very high anatomical resolution. This applies in particular for gadolinium containing contrast media with respect to T1-weighted images. This enables to localize space occupations in small structures such as lymph nodes. Such a high anatomical resolution is not possible with iron contrast medium which becomes visible via susceptibility artefacts in T2-weighted images.

Furthermore, the marker can be such that it is detectable via computer tomography and preferably comprises an iodine compound, including iopromide, thyroxine, triiodothyronine and triiodobenzoic acid.

By this measure such a composition is provided by means of which prostate cells and prostate carcinoma cells, including such in the lymph nodes, can be imaged via computer tomography.

Furthermore, the marker can be such that is detectable by means of nuclear medical methods and preferably comprises a γ-radiator, such as gadolinium-153 or a β-radiator, including Sr-89, Y-90, I-131, Er-169, Re-186 and Re-188.

By this measure such a composition is provided by means of which prostate cells or prostate carcinoma cells, including such being in the lymph nodes, can be imaged within the framework of nuclear medical methods.

It is understood that the composition according to the invention can not only comprise one marker but also several markers. It is possible that the composition according to the invention comprises several molecules of the same marker, for example several Gd-DOTA compounds. Such a compound has the advantage that it results in a particularly strong signal in the magnetic resonance tomography. It is, however, possible that the composition according to the invention comprises several different markers. There could be different markers which are detectable by means of the same imaging method, or different markers which are detectable by means of different imaging methods. The composition according to the invention can, for example, comprise a Gd-DOTA compound and a FITC and/or rhodamine compound. This measure has the advantage that the composition according to the invention can both be detected in the magnetic resonance tomography and in the fluorescence microscopy and in both methods prostate cells or prostate carcinoma cells including such in the lymph nodes can be imaged.

The information given for the marker applies correspondingly for the linker. Thus, the composition according to the invention can comprise several identical or different linkers.

Linker and marker can directly and covalently be linked to each other. Marker and ligand can, however, also be bound to each other via a so-called "linker" which preferably comprises 1, 2, 3, 4, 5, 6, 10, 15 or any number of amino acids. The provision of such an amino acid linker has the advantage that the distance between marker and ligand is increased which has a positive influence on the interaction with the receptor.

Especially suited linkers contain lysine residues since they comprise a free amino group to which the markers or ligands, respectively, can be coupled via a peptide bond. Examples for suitable linkers are the following, wherein it is agreed that the N-terminus is on the left side and the C-terminus is on the right side: lysine-glycine-lysine-glycine, lysine-ahx-lysine-ahx (ahx: amino hexanoic acid), lysine-βala-lysine-βala, glutamic acid.

In this context it is preferred if the composition comprises a compound which is selected from the group consisting of:

(compound 1)

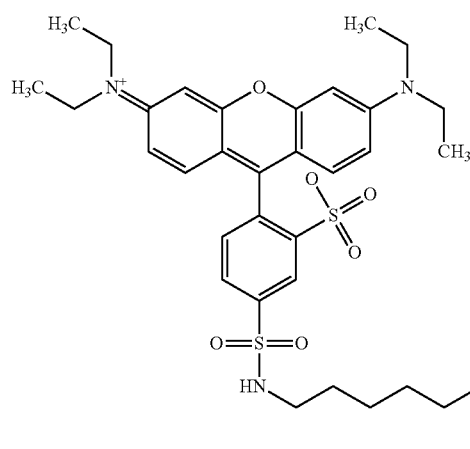

Sulforhodamine-sulfonamido aminoundecyclic aldehyde (compound 2)

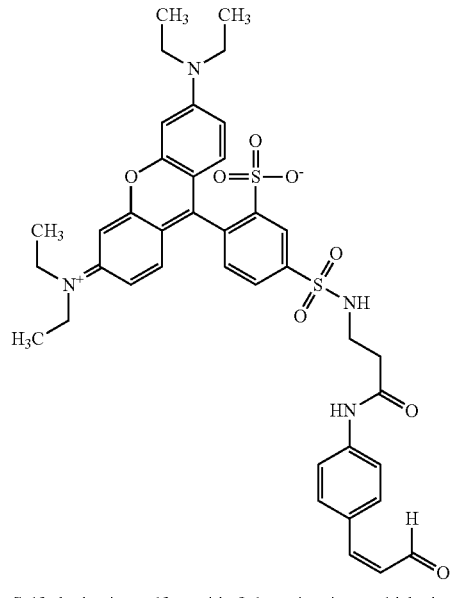

Sulforhodamine-sulfonamido βala-aminocinnamaldehyde (compound 3)

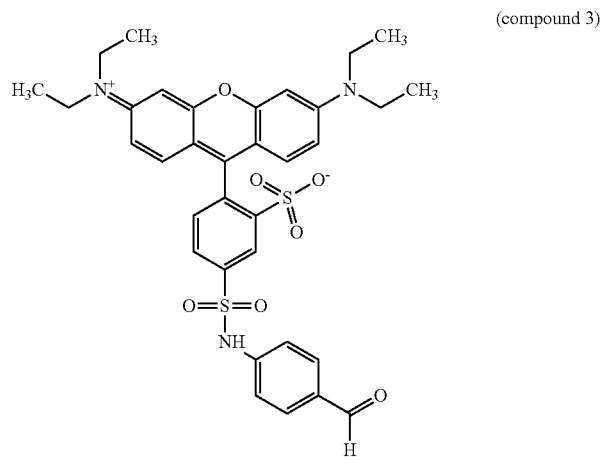

Sulforhodamine-sulfonamido aminobenzaldehyde (compound 4)

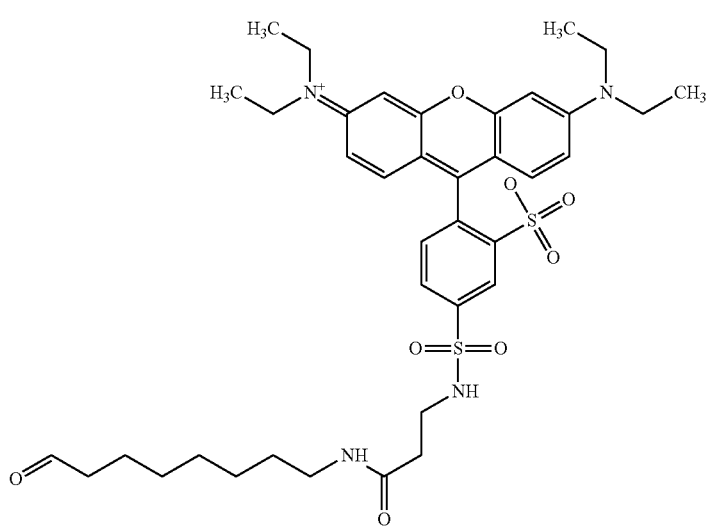

Sulforhodamine-sulfonamido βala-aminooctanal (compound 5)

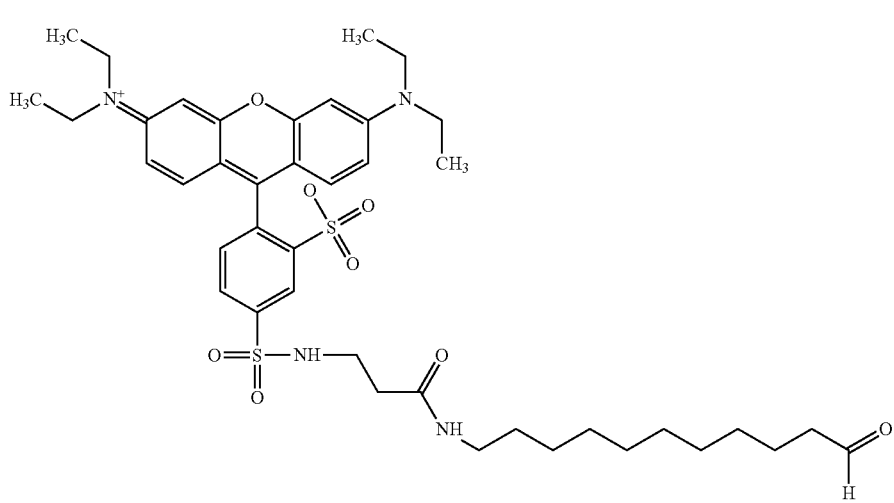

Sulforhodamine-sulfonamido βala-aminoundecylic aldehyde (compound 6)

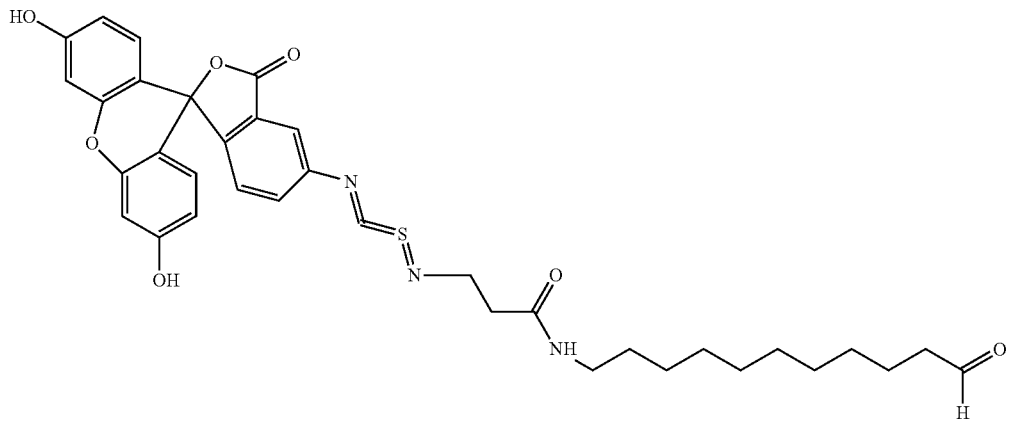

FITC βala-aminoundecylic aldehyde

The before-mentioned compositions comprise the fluorescence markers rhodamine or sulforhodamine and FITC and, therefore, can be detected in the fluorescence microscopy.

The compounds 2, 4, 5, and 6 comprise a linker consisting of an amino acid (alanine), via which the ligand is bound to the marker.

(compound 7)

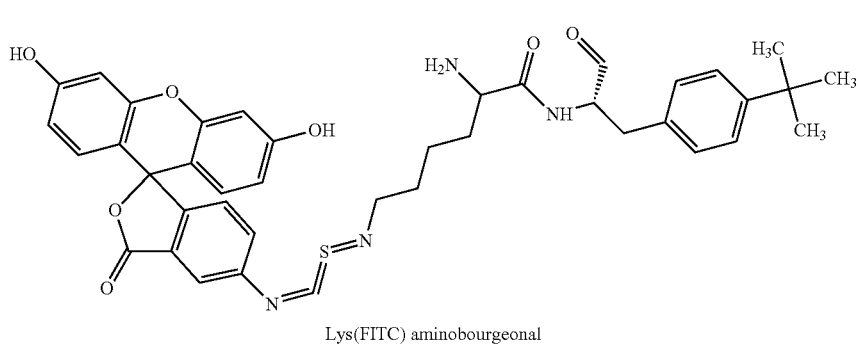

Lys(FITC) aminobourgeonal

The before-mentioned compositions are particularly suited according to the findings of the inventor.

According to a preferred further development the composition according to the invention comprises a compound which is selected from the group consisting of:

(compound 8)

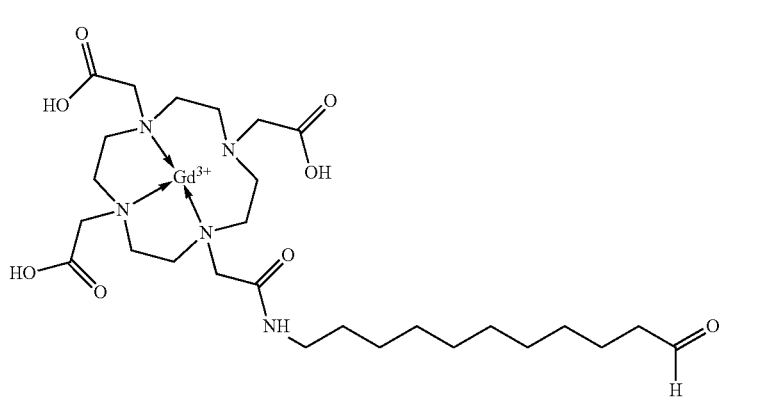

Gd-DOTA aminoundecylic aldehyde (compound 9)

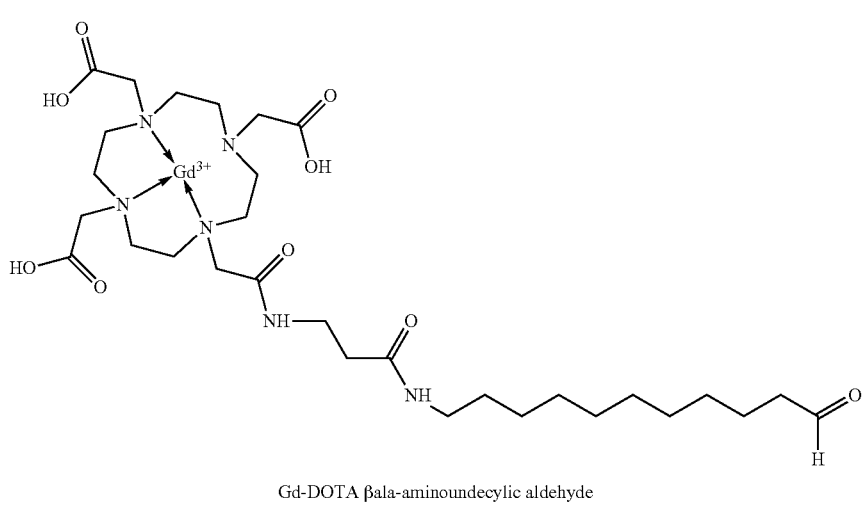

Gd-DOTA βala-aminoundecylic aldehyde

According to the invention, by this measure such compounds are provided which can be used in the magnetic resonance tomography. In the compound 8 the ligand, the undecylic aldehyde or aminoundecylic aldehyde, respectively, is directly linked to the marker Gd-DOTA. In the compound 9 between the ligand and the marker a linker is arranged in form of an amino acid (β-alanine).

According to findings of the inventor the before-identified compositions are particularly suited to image prostate cells or prostate carcinoma cells, respectively, including such being in the lymph nodes, by means of the magnetic resonance tomography.

It is further preferred if the composition comprises a compound which is selected from the group consisting of:
(Verbindung 10)
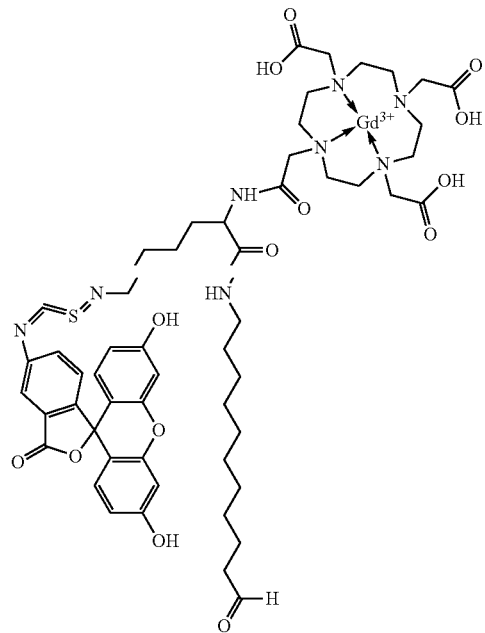
Gd-DOTA-Lys(FITC) aminoundecylic aldehyde
(compound 11)
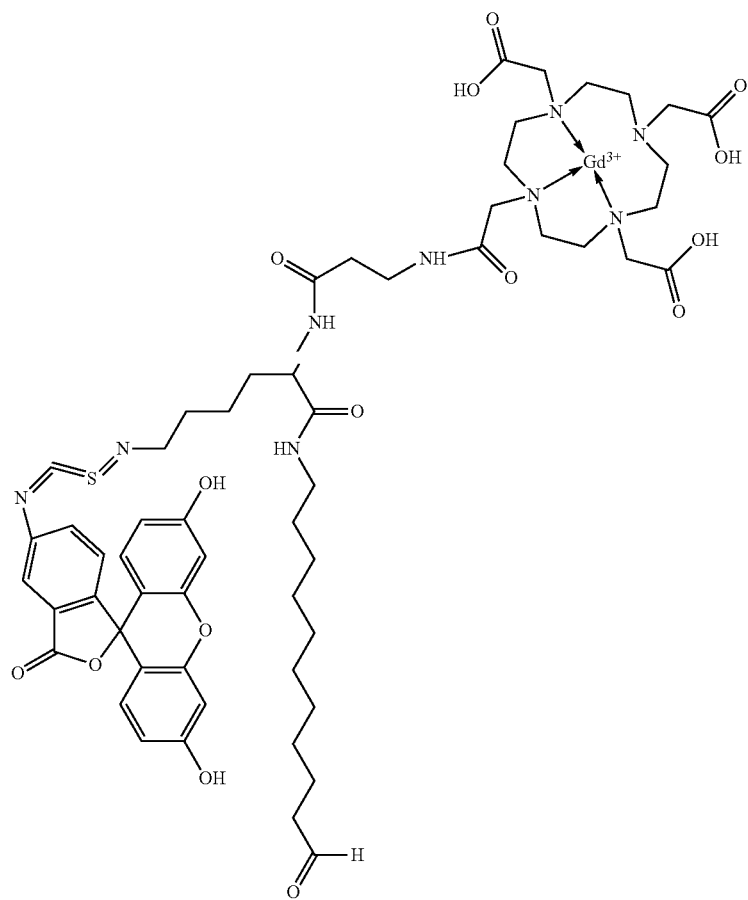
Gd-DOTA βala-Lys(FITC) aminoundecylic aldehyde -continued
(compound 12)
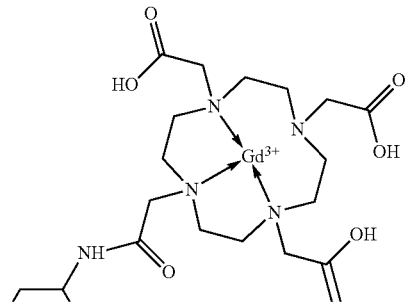
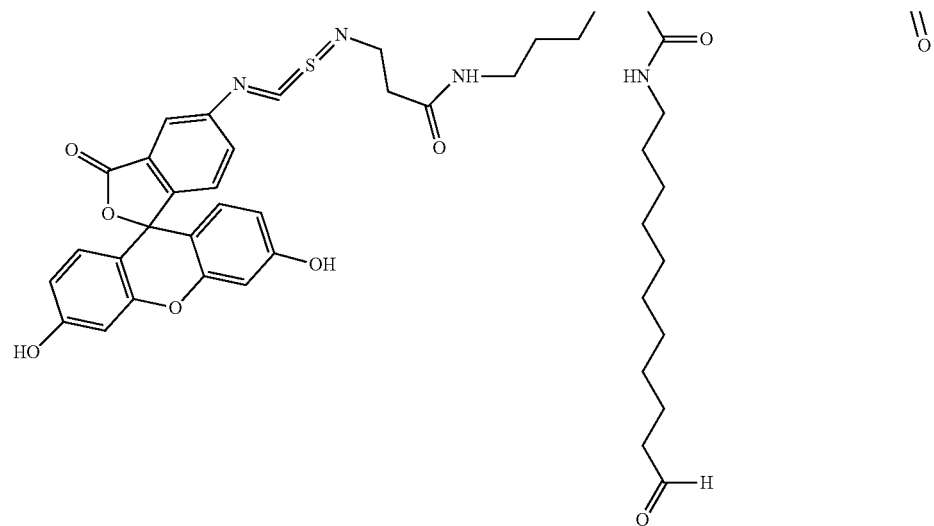
FITC βala-Lys(Gd-DOTA) aminoundecylic aldehyde
(compound 13)
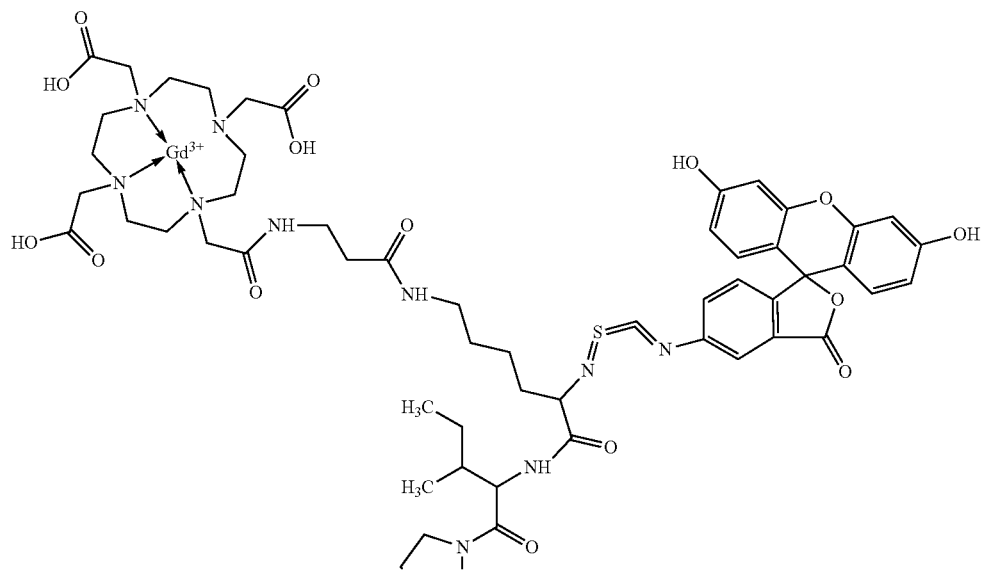

-continued

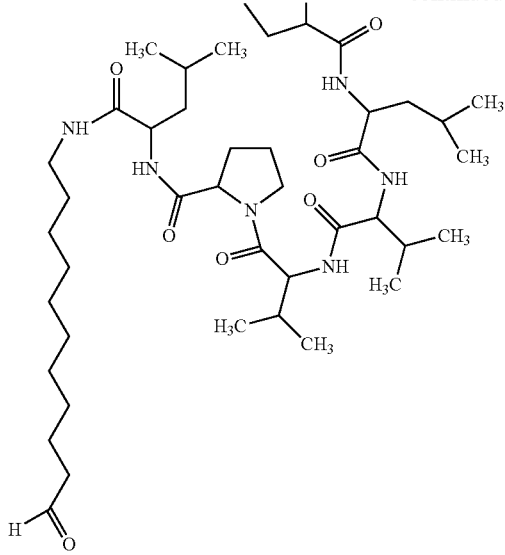

Gd-DOTA βala Lys(FITC)-IPLVVPL aminoendecylic aldehyde (compound 14)

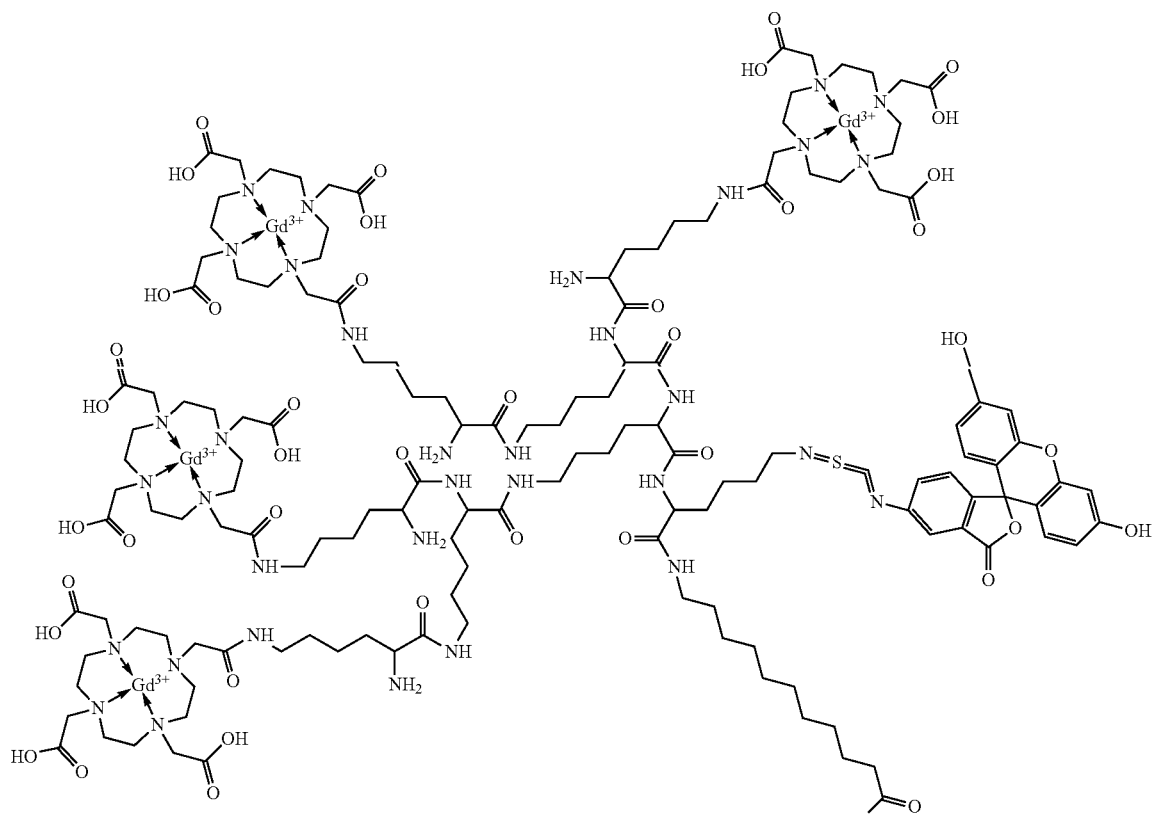

Gd-DOTA(4)-Lys(4)-Lys(2)-Lys(FITC) aminoendecylic aldehyde

By this measure such compositions according to the invention are provided which can be used in the magnetic resonance tomography and also in the fluorescence microscopy. The compositions comprise both a marker detectable in the magnetic resonance tomography, namely Gd-DOTA, and also a marker detectable in the fluorescence microscopy, namely FITC. In the compound 10 the ligand is bound via a lysine residue to the marker Gd-DOTA which is detectable in the magnetic resonance. The fluorescence marker FITC is coupled to the side chain of the lysine residue.

In the compound 11 the ligand is bound via an amino acid linker consisting of alanine and lysine to the MRT marker Gd-DOTA, wherein a FITC marker is coupled to the lysine residue, which is visuable in the fluorescence microscopy.

The compound 12 differs from the compound 10 in that the fluorescence or MRT markers are exchanged with respect to their position.

The compound 13 is characterized in that the ligand is coupled via a linker comprising nine amino acids to the MRT marker, wherein FITC is coupled via the side chain to the lysine residue.

The compound 14 is characterized in that it comprises four Gd-DOTA markers and one FITC marker which are coupled to each other via a linker consisting of seven amino acids. In the magnetic resonance tomography this compound provides a particularly strong signal.

It goes without saying that the before-mentioned compounds are only examples. It is up to the discretion of the skilled person which ligands, which markers and which numbers thereof are coupled to each other in a suitable manner and are provided in form of the composition according to the invention.

The composition according to the invention is preferably a diagnostic composition for the detection of prostate carcinomas.

As the inventor could realize in experiments in vivo with a prostate carcinoma on the nude mouse by using the composition according to the invention the prostate carcinoma tissue could be well stained, whereas the healthy prostate tissue of the mouse showed no noteworthy staining. By means of the composition according to the invention the differenciation between prostate carcinoma tissue and healthy prostate or non-postate tissue is, for this reason, well possible and can be diagnostically used.

By means of the composition according to the invention prostate carcinoma metastases in the lymph nodes and/or the bones can be particularly well imaged. Lymphocytes do not comprise lilly-of-the-valley odorant receptors at their surface and, therefore, cannot bind or absorb the composition according to the invention.

By means of the composition according to the invention a positive imaging of prostate carcinoma cells in lymph nodes has become possible.

The composition according to the invention can also be a therapeutic composition.

Due to the high selectivity and specificity with the composition according to the invention medicaments can be delivered to the prostate cells or prostate carcinoma cells, respectively. This measure has the advantage that the effect exclusively occurs in the prostate cells or prostate carcinoma cells, and other tissue and, therefore, the organism remain spared. Such a therapeutic composition has very few side effects.

Preferably, the composition according to the invention, which adapted as a therapeutic composition, comprises a cytostatic agent which can be realized by a alkylating agent, a platinium analogon, intercalating agent, antibiotic, mitosis inhibitor, texane, topoisomerase inhibitor and antimetabolite.

With this measure such a therapeutic composition is provided by means of which exclusively prostate carcinoma cells can be inhibited and, therefore, killed in a targeted and selective manner. Cells of other tissues remain largely uneffected hereby.

It is understood that the composition according to the invention can be configured as diagnostic composition and also as a therapeutic composition. Therefore, the composition can simultaneously comprise a marker detectable by means of imaging methods and a cytostatic. By this manner the course of the therapy can be visualized.

Against this background another subject matter of the present invention relates to a method for the diagnostic and/or therapeutic treatment of a human being which comprises the following steps: (a) administration of the composition according to the invention into the living being, and (b) performing an imaging method, if applicable, and repetition of step (a), if applicable.

The features, characteristics and advantages of the composition according to the invention apply correspondingly to the method according to the invention.

It is understood that the features of the invention mentioned above and those yet to be explained below can be used not only in the respective combination indicated, but also in other combinations or in isolation, without departing from the scope of the present invention.

The invention is now explained by means of embodiments in more detail resulting in further features, characteristics and advantages. The embodiments are purely illustrative and do not limit the scope of the invention. Reference is made to the enclosed figures.

BRIEF DESCRIPTION OF THE DRAWINGS

FIG. 2D shows LSM images of PC-3-prostate carcinoma cells and U373 glioma cells 48 hours after incubation with Lys(FITC) aminobourgeonal (compound 7).

FIG. 3A shows magnetic resonance tomography images of laterally cutted Eppendorf tubes with LNCaP cells after 20 minutes of incubation with Gd-DOTA alone (DOTAREM) (left) and the Gd-DOTA-Lys(FITC) aminoundecylic aldehyde (compound 10) (right).

FIGS. 3B and C show the influence of the coupling of undecylic aldehyde to Gd-DOTA.

FIG. 3D shows magnetic resonance tomography images of a human PC3 prostate carcinoma in the right lower thigh of a nude mouse (arrow) (10 days after the implantation) before and 90 minutes after the intravenous administration of Gd-DOTA-Lys(FITC) aminoundecylic aldehyde (compound 10).

FIG. 5A shows fluorescence microscopy images of 5 μm frozen sections of a prostate carcinoma (PC3) 20 and 180 minutes after intraperitoneal injection of sulforhodamine sulfonamide aminoundecylic aldehyde (compound 1).

FIG. 5B shows images of a "touch print" of the PC3 prostate carcinoma 20 minutes after intraperitoneal injection of sulforhodamine sulfonamide aminoundecylic aldehyde (compound 1).

DESCRIPTION OF PREFERRED EMBODIMENTS

Figure 1A:
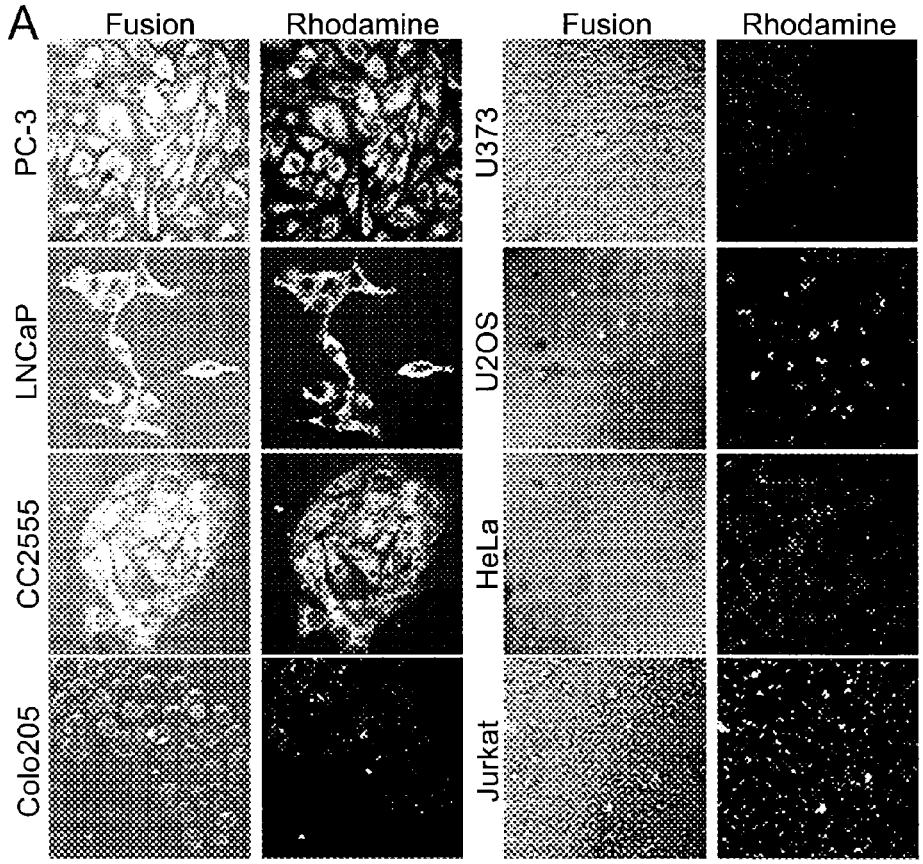
FIG. 1A shows images from the confocal laser scanning micrsocopy (CLSM) of seven human tumor cell lines (PC-3/LNCaP—prostate carcinoma; colo 205—colon carcinoma; U373—glioma; U2OS—osteosarcoma; HeLa—cervix carcinoma; jurkat—lymphoma) and healthy human epithelial prostate cells (CC2555, Lonza) 20 minutes after the incubation with sulfo rhodamine-sulfonamido aminoundecylic aldehyde (compound 1).

1. Material and Methods
1.1 Synthesis of Sulforhodamine-Sulfonamido Aminoundecylic Aldehyde (Compound 1)

Weinreb-AM-resin (NovaBiochem) [0.25 mmol (0.28 g)] was suspended in 10 ml dimethylformamide (DMF) and swelled for 10 minutes. Then the Fmoc protective group is removed by addition of 25% piperidine in DMF (3 minutes, 6 minutes, 2 minutes). After repeated washing steps with DMF three equivalents (0.75 mmol) of Fmoc-aminoundecylic acid are coupled to the resin using 0.75 mmol of TBTU [O-(benzotriazol-1-yl-)-N,N,N',N'-tetramethyluronium tetrafluoroborat] in presence of 6 equivalents of diisopropylethylamin (DIEA) within 1 hour at room temperature.

After repeated Fmoc cleavage 1.5 equivalents of sulforhodamine B acid chloride and 1.5 equivalents of DIEA are dissolved in 1:1 mixture of DMF/dichlormethan, added to the mixture and shaken for 6 hours at room temperature.

The excess dye is then washed off and the peptide resin is suspended in absolute tetrahydrofurane (THF), while the reaction is cooled with ice 2.5 ml of 1M lithium aluminium hydrid solution are added and stirred for 45 minutes.

After hydrolysis by careful addition of 2N citric acid the resin is filtered off and the filtrate is deluted in dichloromethane (DCM). The DCM solution is washed with 2N citric acid and saturated NaCl solution and dried with $Na_2SO_4$. The product is purified by liquid chromatography on a silica gel column using ethylacetate/petroleum ether.

The product is verified by electrospray ionisation mass spectrometry (ESI-MS).
1.2 Synthesis of Sulforhodamine-Sulfonamido βAla-Aminocinnamaldehyde (Compound 2)

The synthesis is realized as under 1.1. Instead of Fmoc-aminoundecylic acid Fmoc-aminocinnamic acid is used.
1.3 Synthesis of Sulforhodamine-Sulfonamide βAla-Aminooctanal (Compound 4)

The synthesis is realized as under 1.1. Instead of Fmoc-aminoundecylic acid Fmoc-aminooctanoic acid is used.
1.4 Synthesis of Lys(FITC)Aminobourgeonal (Compound 7)

The synthesis is realized as under 1.1 and 1.5. Instead of Fmoc-aminoundecylic acid Fmoc-p-tBu-Phe-OH is used.
1.5 Synthesis of DOTA-Lys(FITC) Aminoundecylic Aldehyde and its Gadolinium Complex (Compound 10)

Weinreb-AM-resin (NovaBiochem) [0.25 mM (0.28 g)] is freed from the Fmoc-protective group with 25% piperidine/DMF (3 minutes, 6 minutes, 2 minutes). By coupling of 3 equivalents of Fmoc-aminoundecylic acid with TBTU [O-(benzotriazol-1-yl)-N,N,N',N'-tetramethyluronium tetrafluoroborate] and 6 equivalents of diisopropylethylamine (DIEH) Fmoc-AM-Weinreb-resin is obtained.

After Fmoc cleavage Fmoc-Lys Mmt)-OH is coupled to the resin using TBTU (Mmt: methyloxytrityl). Then the Fmoc-protective group is cleaved off again and DOTA (1.4.7.10 tetraazazyclododecan-1,4,7 tri-tert-butyl acetate-10-acetic acid) is coupled to the lysine with TBTU/DIEA.

The Mmt-protective group is cleaved off by repeated pouring of the resin with 1% trifluor acetic acid solution in dichlormethan within one hour at room temperature, and the resin is then neutralized by addition of DIEA DITC (fluorescein isothiocyanat) is dissolved in DMSO and coupled to the resin overnight in the presence of diisopropylethylamine The excess fluorescein dye is washed out several times and the resin is dried and suspended in THF, cooled down to 5° C. and 2.5 ml of 1 M lithium aluminium hydrid in THF is added and stirred for 45 minutes at room temperature.

The preparation is hydrolysed by carefully adding 2 N citric acid. Then a separation from polymeric compounds occurred and dichlormethane is added. The preparation is washed repeatedly with citric acid and NaCl solution and dried with sodium sulphate.

After the solvent is removed the remaining tert-butyl ester groups are removed by pouring with trifluoracetic acid and stirring for half an hour at room temperature. The trifluor acetic acid is removed and the preparation is dissolved in 10% acetic acid and lyophilized.

The resulting composition is stirred for 5 hours at 50° C. with 1 equivalent of gadolinium-III-chloride hexahydrate in water at pH 5.6 adjusted with NaOH. After an acidification with diluted acetic acid the preparation is relyophilized.

The product is verified by electrospray ionisation mass spectrometry (ESI-MS).
1.6 Electrospray Ionisation Mass Spectrometry (ESI-MS)

The conjugates were analyzed by ESI-MS on an Esquire3000+ Ion Trap Mass Spectrometer (Bruker-Daltonics, Bremen, Germany). The conjugates were taken up in 40% ACN, 0.1% formic acid (Sigma-Aldrich) in water (v/v/v) (20 pmol/μl) and constantly infused using a syringe pump (5 μl/min flow rate). Mass spectra were acquired in the positive ion mode. Dry gas (6 l/min) temperature was set to 325° C., the nebulizer to 20.0 psi, and the electrospray voltage to −3700 V.
1.7 Confocal Laser Scanning Microscopy (CLSM)

The cells were grown to 80% confluency at 37° C., 5% $CO_2$ (vol/vol) in 4-well plates (NUNC, Wiesbaden, Germany) with about 300,000 cells per well.

U373 human glioma cells, human prostate carcinoma cells PC3 and LNCaP, human Jurkat lymphoma cells, and human colon carcinoma cells Colo205 were grown in RPMI1640 ready mix medium containing L-glutamine and 10% fetal bovine serum (FBS)-gold (PAA Laboratories, Pasching, Austria). U2OS human osteosarcoma cells and HeLa human cervix carcinoma cells were grown in high glucose Dulbeccos modified Eagle's medium containing GlutaMax™ and pyrovate and 10% FBS-gold. Healthy human prostate cells (CC2555, Lonza, Verviers, Belgium) were cultivated in prostate endothelial cell growth medium (PrEGM, Lonza, Verviers, Belgium).

The compounds 1, 2 and 4 were dissolved at 1 mg/ml in pure ethanol (Riedel de Haen, Sigma-Aldrich, Taufkirchen, Germany) and then diluted in the appropriate medium for the cells to 10 μg/ml of conjugate and 1% ethanol. The cells were incubated at 37° C. in an atmosphere of 5% $CO_2$ for 20 minutes with the compounds. After this, the cells were rinsed three times with medium and then incubated with medium again. This experiment was also performed with free sulforhodamine B with a corresponding amount.

To illustrate phosphatidylserine (apoptosis test) annexin-fluos (Roche Diagnostics, Mannheim, Germany) was added. This was done after 20 minutes and also after 2 days of incubation with the compounds 1, 2 and 4.

The compound 10 was dissolved in culture medium (260 µM). Lys(FITC)-aminobourgeonal (compound 7) was dissolved in culture medium with 1% ethanol (260 µM). The cells were incubated for 20 minutes (compound 10) and for 2 days (compounds 7 and 10). This assay was also performed with free FITC. After the incubation the cells were rinsed three times with medium and again incubated in medium. Propidium iodide (PI) (molecular probes, Eugene, Oreg., USA) was added to stain death cells.

The confocal laser scanning microscopy was performed on an inverted LSM510 laser scanning microscope (Carl Zeiss) (objective: LD Achroplan 40×0.6, Plan Neofluar 20×0.50, 40×0.75). For the rhodamine fluorescence excitation the 543 nm beam of a helium-neon laser with suitable beam splitters and barrier filters were used. All measures were performed at least three times on living, non-fixed cells.

1.8 Mouse Organ Sections and Touch Prints

PC3 and LNCaP prostate tumor cells were grown to 80% confluency, detached with Accutase™ (PAA Laboratories, Pasching, Austria) and then harvested. The cells were washed with PBS three times and then drawn up into a 30 g Micro-Fine™ insulin syringe (Becton Dickinson, Franklin Lakes, N.J., USA). Approximately $5\times10^5$ cells per mouse were injected into the right thigh of a male CD1 Nu/Nu mouse (Charles River, WIGA, Sulzfeld, Germany). The tumor growth was monitored and after 10 to 14 days mice bearing tumors with 2-3 mm in diameter were treated with the conjugate. 1.5 mg of the compound 1 were dissolved in 300 µl PBS containing 20% ethanol and applied intraperitoneally. After 90 minutes of circulation the mice were sacrificed and subsequently the tumors and organs were removed, embedded in Jung tissue freezing medium (Leica Instruments, Nussloch, Germany) and frozen in liquid nitrogen. Frozen sections (5 µm thickness) were prepared (LD3000 Cryotom, Leica Biosystems GmbH, Nussloch, Germany) and the rhodamine staining was analyzed by confocal laser scanning To evaluate the in- and efflux of the rhodamine conjugated compound 1, the experiment was repeated with circulation times of 20 minutes and 180 minutes.

For touch prints, the tumor of a mouse treated with the rhodamine containing compound 1 (1.5 mg intraperitoneally for 20 minutes) was excised. The tumor was cut and the cells were streaked onto a slide without fixation. The tumor cells were immediately analyzed by CLSM (without fixation).

The experiments were repeated two times.

1.9 Magnetic Resonance Tomography Measurements

The magnetic resonance tomography (MRT) measurements were performed using a clinical 3-Tesla Siemens whole body MRT (Magnetom TRIO; Siemens, Erlangen, Germany) with the mice in prone position in a standard circular polarized wrist coil. The MRT protocol consisted of native and post-contrast T1 weighted axial images: slice thickness 2 mm, field of view read: 60 mm/7.5%, Voxel size: 0.2×0.2×2 mm, repetition time (TR): 800 ms, echo time (TE): 9.1 ms, flip angle: 90°, acquisitions: tions: 2, number of slices: 25, distance factor: 0, scan time 06:02 min.

The DOTA-containing compound 9 was administered to three narcotized mice intravenously via the tale vein (3mg in 200 µl of PBS).

1.10 MR Relaxometry

For the MR relaxometry, all tumor cell lines were grown in 75 cm² culture flasks (Corning Costar, Bodenheim, Germany) (70% confluency). Accutase™ (PAA Laboratories, Pasching, Austria) was added to achieve detachment of the cells, which were harvested and subsequently aliquoted into Eppendorf tubes ($6\times10^6$ cells per tube). The cells in the tubes were incubated with the DOTA-containing compounds (130 µM). After a 20 minutes incubation period at 37° C. in an atmosphere of 5% $CO_2$, the cells were washed three times in PBS and centrifuged at 800 rpm for 5 minutes.

The in-vitro MRT was performed with a 3 Tesla-whole body MRT system (Magnetom TRIO, circular polarized wrist coil, Siemens, Erlangen, Germany)

Sagittal T1-weighted MR images were obtained using the following spin-echo sequence:

Repetition time (TR): 200 ms, echo time (TE): 7,4 ms, flip angle: 90°, averages: 1, concatenations: 2, measurements: 1, number of slices: 19, distance factor: 30%, slice thickness: 3 mm, field of view read: 180 mm/100%, resolution: 256/100%, voxel size: 0.7×0.7×3.0 mm, scan time: 1:48 min.

The T1 relaxation times were evaluated from signal intensities obtained by multiple spin-echo measurements:

Repetition time (TR): 20-8000 ms (50 different TR values), echo time (TE): 6.4 ms, flip angle: 90°, averages: 1, measurements: 1, number of slices: 1, slice thickness: 1 mm, field of view read: 120 mm/87.5%, resolution: 128/100%, voxel size: 0.9×0.9×1 mm.

The analysis and calculations were performed using a Matlab program (Math Works, Natick, Mass., USA). The T1 values were approximated by a three-parameter fit procedure. All signal curves were examined and found to be monoexponential. The investigations were performed in triplicate.

1.11 Flow Cytometry

For the fluorescence activated cell sorting (FACS), cells were grown in 75 cm² culture flasks (Corning Costar, Bodenheim, Germany) (80% confluency) under the same conditions as described for the confocal laser scanning microscopy. Accutase™ (PAA Laboratories, Pasching, Austria) was added to achieve detachment of the cells, which were harvested and subsequently alequoted into Eppendorf tubes (Eppendorf, Hamburg, Germany) ($1\times10^6$ cells per tube). The cells were incubated for 20 minutes with the compounds 1, 2 and 4 (10 µg/ml in the appropriate medium with 1% ethanol) and the compound 10 (130 µM in the appropriate medium).

Afterwards, the cells were washed three times in PBS and centrifuged at 800 rpm for 5 minutes. Then 300 µl FACS buffer (D-PBS containing 1% parafomaldehyde) were added. The samples were measured immediately. Approximately 20,000 events were recorded per sample. The fluorescence excitation was achieved by an argon laser (488 nm). The fluorescence was detected using a 580-610 and a 560-680 nm band-pass filter. All investigations were performed in triplicate.

Mean rhodamine and fluorescein isothiocyanate fluorescence values of the samples were acquired using the WinMDI software (Joseph Trotter, Scripps Research Institute, San Diego, Calif., USA) and then statistically evaluated.

2. Results 2.1 Selective Staining of Prostate Cells In Vitro

Seven human tumor cell lines and healthy human epithelial prostate cells (CC2555) were incubated for 20 minutes with sulforhodamine-sulfonamido-aminoundecylic aldehyde (compound 1) and analyzed by means of confocal laser scanning microscopy (CLSM).

The result is shown in FIG. 1A. There it can be seen that the prostate carcinoma cells (PC-3, LNCaP) and the healthy prostate cells (CC2555) take up the compound according to the invention into the cytoplasm, the cell nuclei are left free. All other cells, however, do not take up the compound according to the invention. Rhodamine without undecylic aldehyde alone is not taken up by any cell types (not shown).

In another approach both the prostate carcinoma cells (LNCaP) as well as the colon carcinoma cells (Colo205) were incubated for 20 minutes with sulforhodamine-sulfonamido βala-cinnamaldehyde (compound 2) and analyzed by CLSM.

Figure 1B:
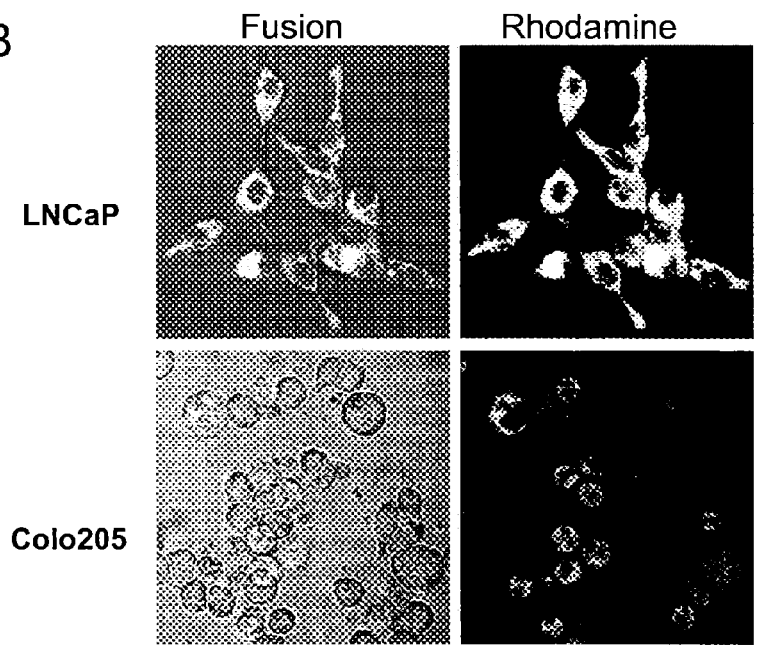
FIG. 1B shows CLSM images of prostate carcinoma cells (LNCaP) and colon carcinoma cells (Colo205) 20 minutes after the incubation with sulfo rhodamine-sulfonamido βala-aminocinnamaldehyde (compound 2).

The result is shown in FIG. 1B. It can be seen that the prostate carcinoma cells are significantly stained, however the colon carcinoma cells remain basically unstained. The compound according to the invention is, therefore, uptaken by the prostate carcinoma cells into the cytoplasm, however not the colon carcinoma cells.

In a further experiment prostate carcinoma cells (PC-3) and osteosarcoma cells (U205) were incubated for 20 minutes with Gd-DOTA-Lys(FITC) aminoundecylic aldehyde (compound 10) and analyzed by CLSM.

Figure 2A:
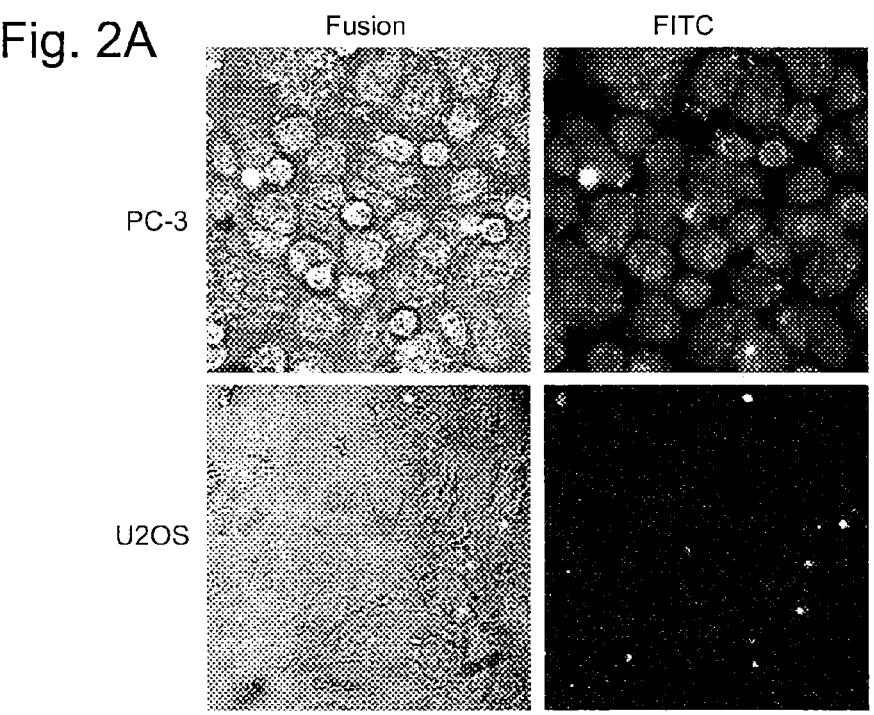
FIG. 2A shows CLSM images of prostate carcinoma cells (PC-3) and osteosarcoma cells (U2OS) 20 minutes after the incubation with Gd-DOTA-Lys(FITC) aminoundecylic (compound 10).

The result is shown in FIG. 2A. Thus, the compound according to the invention is very well uptaken into the cytoplasm of the prostate carcinoma cells, however not into the osteosarcoma cells. FITC alone (without undecylic aldehyde) is not uptaken by the cells (not shown).

Next, seven tumor cell lines and healthy prostate cells (CC2555) were incubated for 20 minutes with Gd-DOTA-Lys (FITC) amino undecylic aldehyde (compound 10) and analyzed by fluorescence activated cell sorting (FACS).

Figure 2B:
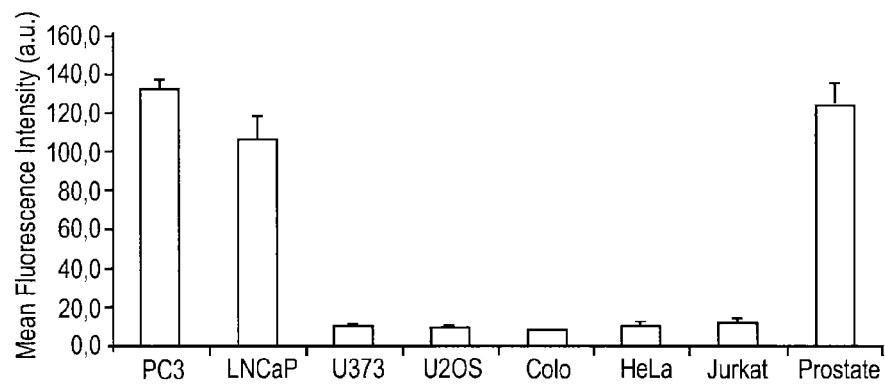
FIG. 2B shows images from the fluorescence activated cell sorting (FACS) of seven tumor cell lines (PC-3/LNCaP—prostate carcinoma; Colo205—colon carcinoma; U373—glioma; U2OS—osteosarcoma; HeLa—cervix carcinoma; Jurkat—lymphoma) and healthy human epithelial prostate cells (CC2555, Lonza) after the incubation with Gd-DOTA-Lys(FITC)-aminoundecylic aldehyde (compound 10) (in triplicate, standard deviation of the mean value).

The result is shown in FIG. 2B. There it can be seen that both of the prostate carcinoma cell lines (PC-3, LNCaP) and the healthy prostate cells (CC2555) are stained, however not the non-prostate tumor cell lines. Thus, only the prostate cells take up the compound according to the invention.

In a further experiment several carcinoma cells were incubated for 20 minutes with sulforhodamine-sulfonamido βala-aminooctanal (compound 4) and analyzed by FACS.

Figure 2C:
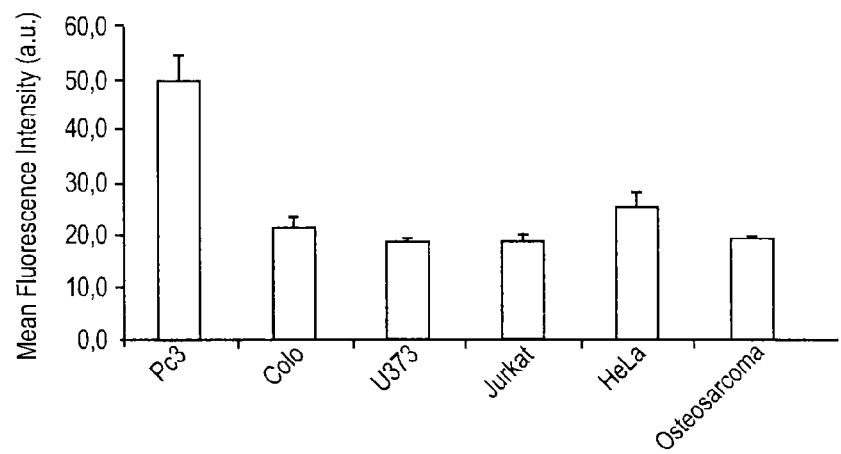
FIG. 2C shows images of a FACS analysis of different carcinoma cells 20 minutes after the incubation with sulforhodamin sulfonamide-βala-aminooctanal (compound 4) (in triplicate, standard deviation of the mean value).

The result is shown in FIG. 2C. There it can be seen that the prostate carcinoma cells (PC3) show the highest fluorescence, i.e. they take up the compound according to the invention. The remaining carcinoma cell lines only show little staining, therefore take up the compound according to the invention only to a small extend.

In another approach U373 glioma cells and PC3 prostate carcinoma cells were incubated for 48 hours with Lys(FITC)-aminobourgeonal (compound 7) and analyzed by CLSM.

The result is shown in FIG. 2D. The prostate carcinoma cells are cytoplasmatically stained, however not the glioma cells. Like the other conjugates no cytotoxic alterations are shown.

In another experiment LNCaP cells were incubated for 20 minutes with Gd-DOTA alone (DOTAREM, Guerbet, France) and with the compound 10 according to the invention Gd-DOTA-Lys(FITC) aminoundecylic aldehyde in an Eppendorf tube and washed out.

The result is shown in FIG. 3A. It turns out that the simple Gd-DOTA compound is not taken up by the prostate carcinoma cells. After the incubation and the washing out the cells remain, therefore, dark; cf. FIG. 3A, left. The Gd-DOTA undecylic aldehyde compound, according to the invention is, however, uptaken into the cytoplasm of the prostate carcinoma cells via the lilly-of-the-valley odorant receptor. After the washing out and centrifugation these cells are, therefore, light; cf. FIG. 3A, right.

2.2 Influence of the Coupling of Undecylic Aldehyde to Gd-DOTA

Six different tumor cell lines (including LNCaP-prostate carcinoma cells) were, on the one hand, incubated in Eppendorf tubes with Gd-DOTA alone (DOTAREM, Guerbet, France), and on the other hand with the compound 10 Gd-DOTA-Lys(FITC) aminoundecylic aldehyde according to the invention and subsequently washed with PBS for three times.

The result is shown in FIG. 3B. The Eppendorf tubes are transversely cut. In the right column the prostate carcinoma cells (LNCaP) as also all of the other carcinoma cells remain dark after the incubation and washing out with the simple Gd-DOTA compound. Only after incubation with the compound 10 Gd-DOTA-Lys(FITC) aminoundecylic aldehyde according to the invention an increase of the signal intensity occurs, however only with the LNCaP-prostate carcinoma cells; cf. FIG. 3B, left column, top.

The coupling of undecylic aldehyde to Gd-DOTA (left column), therefore, results in a significantly stronger T1-time reduction for prostate carcinoma cells in comparison to simple Gd-DOTA (right column), however not for the other tumor cell lines. The reduction of the T1-time indicates the increase of the brightness (signal intensity) in the cells which is effected by the cellular uptake of a gadolinium compound in the T1-weighted images.

In FIG. 3C the bars indicate the difference of the T1-time of the respective carcinoma cells and the healthy prostate cells (CC2555) after the incubation with the compound 10 Gd-DOTA-Lys(FITC) aminoundecylic aldehyde according to the invention and the simple Gd-DOTA compound. The difference of the T1-time indicates to which extend the compound in a respective cell line results in a reduction of the T1-time (increase of the brightness, signal intensity). This unit is used since the cell lines have different T1-times before the incubation. Difference of the T1-time=(T1-time before the incubation) minus (T1-time after the incubation). The T1-time before the incubation is longer than after the incubation. The shorter the T1-time the lighter the cells.

As can be taken from the drawing of FIG. 3C the PC-3 and LNCaP-prostate carcinoma cells and the healthy prostate cells (CC2555) show the strongest increase of the signal intensity in the T1-weighted MRT-images (strongest reduction of the T1-time, largest difference between the T1-time before and after incubation, in relation to the brightness value at the beginning before the incubation).

2.3 Selective Uptake of the Compounds According to the Invention Into the Prostate Carcinoma In vivo In another experiment with a nude mouse having a human PC3-prostate carcinoma implanted into the right thigh, 10 days after the implantation the compound 10 Gd-DOTA-Lys (FITC) aminoundecylic aldehyde according to the invention was intravenously administered.

The result before and 90 minutes after the intravenous administration is shown in FIG. 3D. It turns out that it is only absorbed into the cytoplasm of the prostate-carcinoma cells which are then shown with an increased signal intensity. Non-prostate carcinoma cells remain unstained, thus do not uptake the compound according to the invention.

In another experiment organs of nude mice, into which a human prostate carcinoma (PC-3) was implanted, were analyzed by means of frozen sections 90 minutes after the intraperitoneal injection of the compound 1 sulforhodamine-sulfonamido aminoundecylic aldehyde according to the invention by CLSM.

Figure 4:
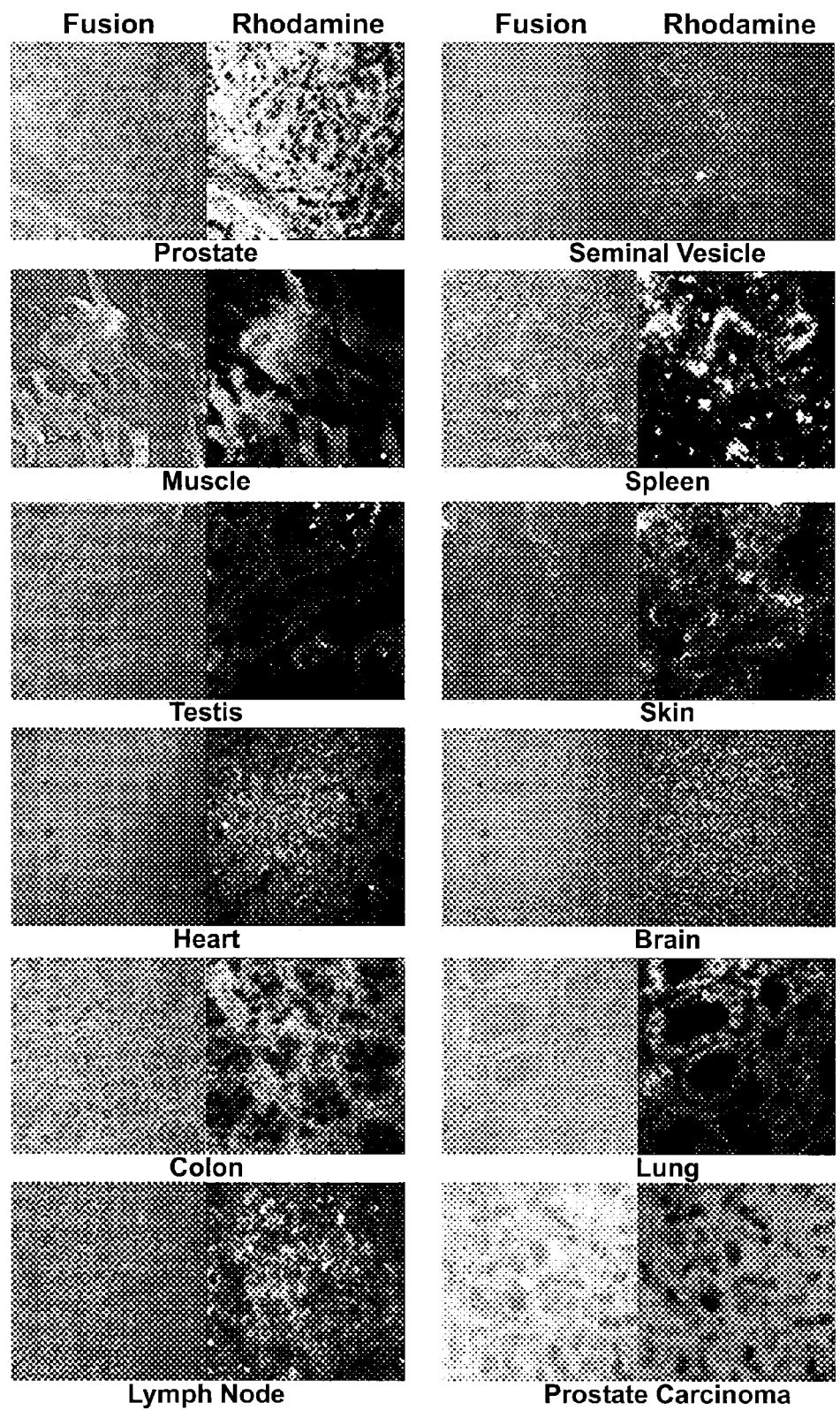
FIG. 4 shows CLSM images of 5 µm frozen sections of nude mice organs and a human prostate carcinoma (PC3) 90 minutes after the intraperitoneal injection of sulforhodamine sulfonamide aminoundecylic aldehyde (compound 1) (in each case, superposition of the transmission and rhodamine channel on the left, only rhodamine channels on the right).

The result is shown in FIG. 4. It turns out that, in comparison to possible areas of metastases such a lymph nodes and the lung, the prostate carcinoma shows a significantly stronger red fluorescence. Interestingly, here also in healthy prostate tissue almost no staining can be observed. Thus, the compound according to the invention is almost exclusively uptaken by prostate carcinoma cells.

In another experiment frozen sections of the prostate carcinoma (PC-3) implanted into nude mice were analyzed 20 and 180 minutes after the intraperitoneal injection of compound 1 sulforhodamine-sulfonamido aminundecylic aldehyde according to the invention.

The result is shown in FIG. 5A. It turns out that the prostate carcinoma cells have already after 20 minutes very well absorbed the compound according to the invention into the cytoplasm. After 180 minutes, however, an efflux of the compound out of the cytoplasm of the prostate carcinoma cells is taken place. The export explains why the compound according to the invention is very well tolerated by the animals.

In FIG. 5B "touch prints" of the PC-3 prostrate carcinoma 20 minutes after the intraperitoneal injection are shown. For this purpose the cells of a freshly cut tumor are streaked onto a slide. In doing so freezing artefacts or artefacts due to the fixation by means of formalin can be excluded. This experiment, therefore, confirms that already 20 minutes after the intraperitoneal injection the compound according to the invention has reached the cytoplasm of the prostate carcinoma cells.

3. Conclusion

With the present invention a composition for the direct and reliable detection of prostate cells or prostate carcinoma cells is provided for the very first time. This composition comprises at least a ligand of the lilly-of-the-valley odorant receptor (OR17-4 or hOR17-4, respectively), optionally a marker detectable by means of imaging methods. The invention is exemplarily demonstrated by means of five different compounds.

The invention claimed is:

1. A method for manufacturing a composition for identifying and treating prostate cells comprising
   a) providing a ligand of lilly-of-the-valley odorant receptor (OR17-4), wherein the ligand of OR17-4 is undecylic aldehyde, and
   b) formulating said ligand of OR17-4 into a pharmaceutically acceptable carrier, wherein the composition further comprises a marker selected from the group consisting of
   a fluorescence marker detectable by means of fluorescence microscopy, wherein the fluorescence marker is selected from fluorescein isothiocyanate (FITC), rhodamine, rhodamine isothiocyanate (RITC), sulforhodamine B, dansyl chloride, fluorescamine, green fluorescent protein (GFP), ethidium bromide, 4'-6-diamidino-2- phenylindole (DAPI), coumarin, luciferase, phycoerythrin (PE), Cy2, Cy3.5, Cy5, Cy7, texas red, alexa fluor, fluor X, red 613, BODIPY-FL, TRITC, and DS red,
   a magnetic resonance tomography (MRT) marker detectable by means of magnetic resonance tomography (MRT), wherein the MRT marker comprises a complexing agent for metals and a complexed metal, said complexed metal is selected from gadolinium (Gd), europium (Eu), gallium (Ga), manganese (Mn), iron (Fe), yttrium (Y), and its isotopes,
   a computer tomography (CT) marker detectable via computer tomoraphy, wherein said CT marker comprises an iodine compound selected from iopromide, thyroxine, triiodothyronine, and triiodobenzoic acid,
   and a radioactive marker detectable by means of nuclear medical methods, wherein the radioactive marker is the γ-radiator gadolinium-153 or a β-radiator selected from Sr-89, Y-90, 1-131, Er-169, Re-186, and Re-188.

2. Method according to claim 1, wherein the lilly-of-the-valley odorant receptor is human hOR17-4.

3. Method according to claim 1, wherein the complexing agent for metals is selected from the group consisting of:
   tetraazacyclododecane tetraacetic acid (DOTA), diethylenetriaminepentaacetic acid (DTPA), BOPTA, EOB-DTPA, DTPA-DMA, HP-DOBA, DTPA-BMEA, HIDA, DTDP, porphyrine, texaphyrine, TEKES, Fullerene, crown ether.

4. Method according to claim 1, wherein the marker is selected from the group consisting of:
   sulforhodaminesulfonamido aminoundecylic, sulforhodaminesulfonamido-βala-aminocinnamaldehyde, sulforhodaminesulfonamido-aminobenzaldehyde, sulforhodaminesulfonamido-βala-aminooctanal, sulforhodaminesulfonamido-βala-aminoundecylic aldehyde, FITC-βala-aminoundecylic aldehyde and lys(FITC)-aminobourgeonal.

5. Method according to claim 1, wherein the marker is selected from the group consisting of:
   Gd-DOTA-aminoundecylic aldehyde, Gd-DOTA-βala-aminoundecylic aldehyde.

6. Method according to claim 1, wherein the marker is selected from the group consisting of: Gd-DOTA-lys(FITC)-aminoundecylic aldehyde, Gd-DOTA-βala-lys(FITC)-aminoundecylic aldehyde, FITC-βala-lys(FITC)-IPLVVPL-aminoundecylic aldehyde and Gd-DOTA(4)-lys(4)-lys(2)-lys(FITC)-aminoundecylic aldehyde.

7. Method according to claim 1, wherein the composition is a diagnostic composition for the detection of prostate carcinoma.

8. Method according to claim 1, wherein the composition is a diagnostic composition for the detection of prostate carcinoma metastases.

9. Method according to claim 8, wherein the prostate carcinoma metastases are in the lymph nodes and/or bones.

10. Method according to claim 1, wherein the composition is a therapeutic composition.

11. Method according to claim 10, wherein the therapeutic composition comprises a cytostatic agent.

12. Method according to claim 11, wherein the cytostatic agent is selected from the group consisting of: alkylating agents, platinium analogues, intercalating agents, antibiotics, mitosis inhibitors, taxanes, topoisomerase inhibitors and antimetabolites.

13. A method for manufacturing a therapeutic composition for treating prostate cells comprising
    a) providing a ligand of lilly-of-the-valley odorant receptor (OR17-4), wherein the ligand of OR17-4 is undecylic aldehyde, and a cytostatic agent, and
    b) formulating said ligand of OR17-4 and cytostatic agent into a pharmaceutically acceptable carrier.

14. The method of claim 13, wherein the cytostatic agent is selected from the group consisting of: alkylating agents, platinium analogues, intercalating agents, antibiotics, mitosis inhibitors, taxanes, topoisomerase inhibitors and antimetabolites.

* * * * *

UNITED STATES PATENT AND TRADEMARK OFFICE
CERTIFICATE OF CORRECTION

PATENT NO. : 8,691,183 B2
APPLICATION NO. : 13/023136
DATED : April 8, 2014
INVENTOR(S) : Stefan Heckl It is certified that error appears in the above-identified patent and that said Letters Patent is hereby corrected as shown below:

In the Claims:

Claim 1, at Column 25, lines 51-54:

"a computer tomoraphy (CT) marker detectable via computer tomoraphy, wherein said CT marker comprises an iodine compound selected from iopromide, thyroxine, triiodothyronine and triiodobenzoic acid,"

should read

--a computer tomography (CT) marker detectable via computer tomography, wherein said CT marker comprises an iodine compound selected from iopromide, thyroxine, triiodothyronine and triiodobenzoic acid,--

Signed and Sealed this
Seventeenth Day of June, 2014

Michelle K. Lee
*Deputy Director of the United States Patent and Trademark Office*